United States Patent [19]

Etter

[11] Patent Number: 5,101,817
[45] Date of Patent: Apr. 7, 1992

[54] AIRWAY ADAPTER FOR USE WITH CLOSED SUCTION CATHETER SYSTEM

[75] Inventor: Jeffrey W. Etter, San Leandro, Calif.

[73] Assignee: Nellcor, Inc., Hayward, Calif.

[21] Appl. No.: 549,903

[22] Filed: Jul. 9, 1990

Related U.S. Application Data

[63] Continuation-in-part of Ser. No. 389,853, Aug. 4, 1989.

[51] Int. Cl.⁵ ............................................. A61M 16/00
[52] U.S. Cl. ........................... 128/200.26; 128/207.14; 128/912; 128/DIG. 26
[58] Field of Search ...................... 128/200.26, 207.14, 128/207.15, 207.16, 912, DIG. 26, 719

[56] References Cited

U.S. PATENT DOCUMENTS

| | | | |
|---|---|---|---|
| 4,291,691 | 9/1981 | Cabal et al. | 128/912 |
| 4,456,014 | 6/1984 | Buck et al. | 128/719 |
| 4,838,255 | 6/1989 | Lambert | 128/207.16 |

Primary Examiner—Edgar S. Burr
Assistant Examiner—Aaron J. Lewis
Attorney, Agent, or Firm—Townsend and Townsend

[57] ABSTRACT

A gas analyzer airway adapter that permits insertion of a suction tube into the patient without removal of the airway adapter from the patient. The adapter body has three ports. A patient port is formed in the main section of the adapter body and has a fitting that attaches to the endotracheal tube. A sample port is formed in a smaller diameter passage extending from the main body and attaches to the sample intake of a gas analyzer. The central axis of the smaller diameter passage is preferably parallel to the central axis of the main body of the adapter. Finally, a ventilator port is formed in a passage whose central axis extends at approximately a 31 degree angle from the central axis of the main body. A hub/filter assembly is disposed in the smaller diameter passage of the airway adapter, and a longitudinal filter extends into the main body of the adapter. A tube guide is disposed below the filter within the main body of the adapter. The purpose of the guide is to protect the longitudinal filter and to direct the movement of the suction tube as discussed below.

7 Claims, 1 Drawing Sheet

AIRWAY ADAPTER FOR USE WITH CLOSED SUCTION CATHETER SYSTEM

This application is a continuation-in-part of U.S. patent application Ser. No. 389,853, filed Aug. 4, 1989, pending.

BACKGROUND OF THE INVENTION

The present invention relates generally to gas sampling with an airway adapter providing a connection between an endotracheal tube, an artificial breathing system and a gas sample analyzer. In particular, this invention relates to an airway adapter that permits the use of a closed suction catheter system on the patient without disconnecting the gas analyzer from the patient.

During surgery or in an intensive care unit, patients may be mechanically ventilated through an endotracheal tube. Since it is often desirable to measure the mechanical and chemical characteristics of the gases going to and coming from the patient, an airway adapter may be inserted in the line between the patient's endotracheal tube and the ventilator to provide a gas sample port for the gas analyzer. Some earlier designs of airway adapters are described in U.S. patent application Ser. No. 389,853, filed Aug. 4, 1989.

It is sometimes necessary to remove mucus or other material from the patient's mouth, trachea, and other air passages. One removal method is to draw the material into a suction tube inserted into the patient's trachea through the endotracheal tube. These systems are called closed suction catheter systems or closed tracheal suction systems. One such system is the model 2205 system sold by Ballard Medical Systems.

If the gas going to and from the patient must be sampled and analyzed during ventilation, an adapter must be inserted in the line between the ventilator and the endotracheal tube to provide a gas sample port. A filter may be disposed in the airway adaptor to prevent foreign matter from entering the gas analyzer. In airway adapters according to some earlier designs, the filter lies in the flow path between the endotracheal tube and the ventilator.

If a suction catheter system is connected to a gas analyzer adapter of this configuration, however, the adapter's filter will block the path of the suction tube. Thus, in order to insert the suction tube into the patient, the gas analyzer adapter must first be removed from the endotracheal tube. In addition to requiring an extra operational step in a busy operating room or intensive care unit the removal of the adapter interrupts the flow of oxygen and/or anesthetic to the patient.

SUMMARY OF THE INVENTION

This invention provides a gas analyzer airway adapter that permits insertion of a suction tube into the patient without removal of the airway adapter from the patient. The adapter body has three ports. A patient port is formed in the main section of the adapter body and has a fitting that attaches to the endotracheal tube. A sample port is formed in a smaller diameter passage extending from the main body and attaches to the sample intake of a gas analyzer. The central axis of the smaller diameter passage is preferably parallel to the central axis of the main body of the adapter. Finally, a ventilator port is formed in a passage whose central axis extends at an oblique angle from the central axis of the main body.

A hub/filter assembly is disposed in the smaller diameter passage of the airway adapter, and a longitudinal filter extends into the main body of the adapter. The filter and hub are preferably substantially as described in patent application Ser. No. 389,853. A tube guide is disposed below the filter within the main body of the adapter. The purpose of the guide is to protect the longitudinal filter and to direct the movement of the suction tube as discussed below.

To use the airway adapter of this invention with a suction catheter system, the adapter ventilator port is connected to the patient port of the suction system's multiway connector. As the suction tube advances through the multiway connector into the airway adapter the leading end of the tube meets the adapter tube guide. The guide prevents the tube from hitting the filter and guides the tube toward the endotracheal tube at the adapter's patient port. Thus, the airway adapter of this invention permits insertion of the suction tube without interrupting the operation of the gas analyzer.

For a fuller understanding of the nature and advantages of the invention, reference should be made to the ensuing detailed description taken in conjunction with the accompanying drawings.

DETAILED DESCRIPTION OF THE PREFERRED EMBODIMENT

Figure 1:
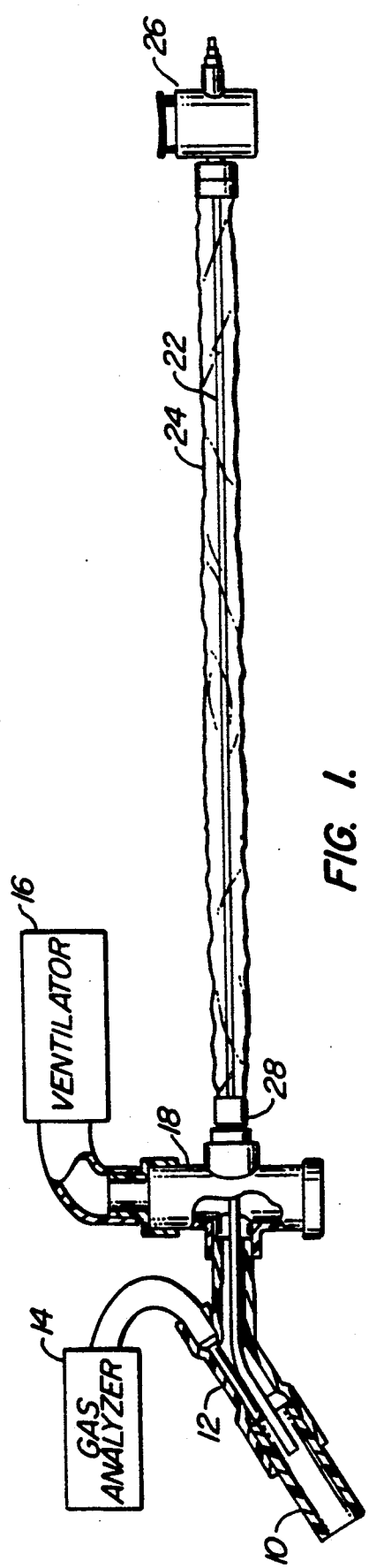
FIG. 1 is a side view of an endotracheal tube ventilator system with an internal suction tube incorporating the present invention.

FIG. 1 shows an endotracheal tube 10 which is inserted in a patient's throat. This is coupled to an airway adapter 12 according to the present invention. Adapter 12 is used to provide a gas sample to an analyzer 14. The gas is provided by a ventilator 16 through a joint 18, through adapter 12 and down tube 10 to the patient.

Since it may be desirable to apply suction to the patient while he is also being ventilated, a closed suction system is used, such as the model 2205 system sold by Ballard Medical Systems.

The Ballard closed suction catheter system consists of a suction tube 22 surrounded by a flexible airtight casing 24. A suction source fitting 26 is attached to one end of the suction tube and casing, and a locking fitting 28 is attached to the other end of the flexible casing. The locking fitting 28 loosely surrounds the suction tube so that the suction tube can slide through the locking fitting. The locking fitting 28 attaches to multiway connector 18, which connects the suction catheter system with the patient's endotracheal tube 10 through adapter 12 and with the mechanical ventilator 16.

To use the Ballard system, the suction tube 22 is advanced through the locking fitting 28, through the multiway connector 18 and down into the endotracheal tube 10. The flexible casing 24 collapses as the suction tube 22 advances, and the slack gathers in front of the locking fitting 28. The flexible casing separates the user's fingers from the suction tube to keep the suction tube sterile. When the leading end of the suction tube is in place within the patient, a vacuum is applied to the suction tube to remove mucus and other matter from the patient.

Figure 2:
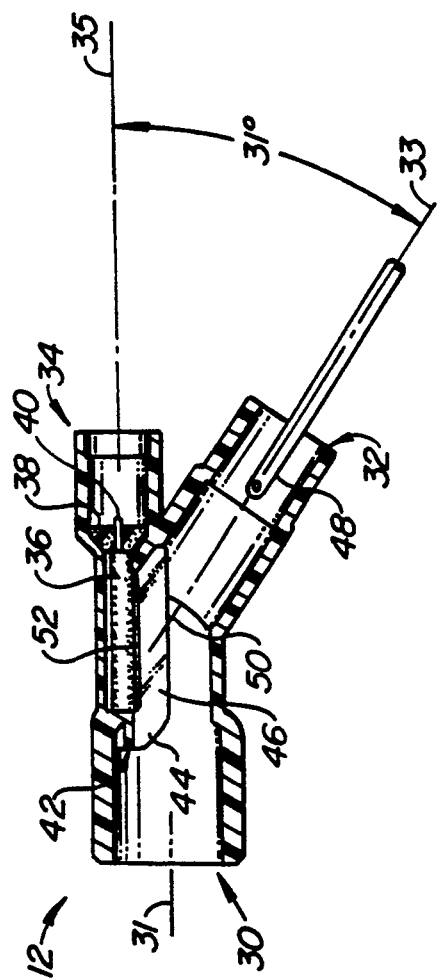
FIG. 2 is a detailed, perspective view of the airway adapter of FIG. 1 according to the present invention.

Airway adapter 12 of FIG. 1 is shown in more detail in FIG. 2. A first, patient port 30 connects to endotracheal tube 10 for insertion into a patient's mouth. A second, ventilator port 32 connects to multiway connector 18 as shown in FIG. 1. The ventilator port 32 has a fitting that can mate with the ventilator inlet or the multiway connector 18 of the suction catheter system. A third, sample port 34 is used for sampling the gas applied to the patient. The axis 33 of port 32 is at an oblique angle, preferably 31°, to the axis 31 of port 30. The axis 35 of port 34, which is parallel to the axis 31 of port 30, is thus at an oblique angle of 31° to the axis 33 of port 32.

An elongate filter 36 extends into the adapter from port 34. Filter 36 extends over an internal hub which is anchored to a disk-shaped seal 38. Gas is drawn through an opening 40 through a tube assembly (not shown) to gas analyzer 14 of FIG. 1. The construction of the filter and tube assembly is shown in more detail in copending application Ser. No. 389,853, filed Aug. 4, 1989, and hereby incorporated herein by reference.

As can be seen, filter 36 extends along an axis of port 34 which is parallel to the axis of port 30. This ensures maximum contact with the gas going through the adapter, thereby giving a good gas sample.

Immediately below filter 36 is a tube guide 42. Tube guide 42 is V-shaped with two planar wings, 44 and 46. When a suction tube 48 is inserted through the adapter, it will contact the inside of the V of tube guide 42 and be redirected out through port 30 as indicated by dotted line 50.

There is a slot 52 at the joint portion of the V of tube guide 42. This slot allows the gas to pass through the tube guide to filter 36. Although the gas can also pass around tube guide 42, the slot provides for additional gas flow. The width of the slot is less than the diameter of suction tube 48 so that the suction tube does not become lodged in the slot.

The structure of adapter 12 uniquely provides the ability for an elongate filter to properly sample the gas being provided to a patient, while at the same time avoiding having the filter interfere with the insertion of the suction tube. The sampling port is arranged at a low angle to the path of the gas from the second port to the first port. Also, a tube guide is used to protect the filter.

As will be understood by those familiar with the art, the present invention may be embodied in other specific forms without departing from the spirit or essential characteristics thereof. For example, the filter could have a different shape, such as a disk shape. The tube guide could be rounded rather than V-shaped. The first and second ports could be axially aligned, with the third port being at a slight angle. The angle is described as oblique (not parallel or perpendicular) because it could be an acute angle (such as 31°) or an obtuse angle, such as 149°. Accordingly, the disclosure of the preferred embodiment of the invention is intended to be illustrative, but not limiting, of the scope of the invention which is set forth in the following claims.

What is claimed is:

1. An airway adapter for use in a system for intubating a patient, comprising:

an adapter body having a first port for connecting to a patient's endotracheal tube, a second port for connecting to a source of gas, and a third port for providing a gas sample;

a gas sampling assembly including an elongate filter extending into said adapter body from said third port; and guide means, mounted in said adapter body between said filter and said second port, having a surface for redirecting a suction tube inserted through said second port away from said gas sampling assembly to said first port and being structured to allow gas from said first and second ports to pass over said filter.

2. The adapter of claim 1 wherein an axis of said third port is substantially parallel to said axis of said first port and said filter is a elongate filter extending along said axis of said third port.

3. The adapter of claim 1 wherein said guide means comprises a pair of planar members joined at first ends and forming an elongate V-shape with an open end of said V-shape disposed in said adapter body to intercept said suction tube.

4. The adapter of claim 1 wherein said filter extends into said adapter body from said third port at an oblique angle to an axis of said second port.

5. The adapter of claim 4 wherein said oblique angle is approximately 31°.

6. An airway adapter for use in a system for intubating a patient, comprising:

an adapter body having a first port for connecting to a patient's endotracheal tube, a second port for connecting to a source of gas, and a third port for providing a gas sample;

a filter extending into said adapter body from said third port at an oblique angle to an axis of said second port; and guide means for directing a suction tube inserted through said second port to said first port without contacting said filter.

wherein said guide means comprises a pair of planar members joined at first ends and forming an elongate V-shape with an open end of said V-shape disposed in said adapter body to intercept said suction tube.

7. An airway adapter for use in a system for intubating a patient, comprising:

an adapter body having first port for connecting to a patient's endotracheal tube, a second port for connecting to a source of gas, and a third port for providing a gas sample;

a gas sampling assembly extending into said adapter body from said third port; and guide means for directing a suction tube inserted through said second port to said first port without contacting said gas sampling assembly, wherein said guide means comprises a pair of planar members joined at first ends and forming an elongate V-shape with an open end of said V-shape disposed in said adapter body to intercept said suction tube, wherein said planar members form a slot along said first joined ends to allow the passage of gas to said filter, said slot having a width smaller than the diameter of said suction tube.

* * * * *